United States Patent [19]

Seward et al.

[11] Patent Number: 5,325,860

[45] Date of Patent: Jul. 5, 1994

[54] ULTRASONIC AND INTERVENTIONAL CATHETER AND METHOD

[75] Inventors: James B. Seward; Abdul J. Tajik, both of Rochester, Minn.

[73] Assignee: Mayo Foundation for Medical Education and Research, Rochester, Minn.

[21] Appl. No.: 790,580

[22] Filed: Nov. 8, 1991

[51] Int. Cl.$^5$ .............................................. A61B 8/12
[52] U.S. Cl. ........................... 128/662.06; 128/660.03
[58] Field of Search ...................... 128/660.03, 662.06; 604/96–103

[56] References Cited

U.S. PATENT DOCUMENTS

| | | | |
|---|---|---|---|
| 4,582,067 | 4/1986 | Silverstein | 128/662.06 |
| 4,794,931 | 1/1989 | Yock | 128/662.06 |
| 4,841,977 | 6/1989 | Griffith et al. | 128/660.03 |
| 4,887,605 | 12/1989 | Angelsen et al. | 128/660.03 |
| 4,911,170 | 3/1990 | Thomas, III et al. | 128/662.06 |
| 4,936,281 | 6/1990 | Stasz | 128/662.06 |
| 4,947,852 | 8/1990 | Nassi et al. | 128/662.06 |
| 4,951,677 | 8/1990 | Crowley et al. | 128/662.06 |
| 4,957,111 | 9/1990 | Miller | 128/662.06 |
| 5,002,059 | 3/1991 | Crowley et al. | 128/662.06 |
| 5,022,399 | 6/1991 | Biegeleisen | 128/662.06 |
| 5,038,789 | 8/1991 | Frazin | 128/662.06 |

OTHER PUBLICATIONS

Masahito Moriuchi et al.: Transvenous Echarcardiography Experimental Feasibility Study. Published on Jpn. Med. Ultrasonic in 1992, vol. 19, No. 3, pp. 229–235. (Exhibit I).

Pandian, N. G. et al., "Intracardiac Echocardiography. Experimental Observations on Intracavitary Imaging of Cardiac Structures with 20-MHz Ultrasound Catheters", Echocardiography, vol. 8: pp. 127–134, Jan. 1991. (Exhibit A).

Seward, J. B. et al., "Transvacular and Intracardiac Two-Dimensional Echocardiography", Echocardiography, vol. 7, Jul. 1990. (Exhibit B).

Schwartz, S. L., (Pandian), et al.: Real-Time Intracardiac Two-Dimensional Echocardiography: An Experimental Study of In Vivo Feasibility, Imaging Planes, and Echocardiographic Anatomy. Echocardiography, 7:4443–455, 1990. (Exhibit C).

Pandian, N. G., et al.: Transvacular and Intracardiac Two-Dimensional High-Frequency Ultrasound Imaging of Pulmonary Artery and Its Branches in Humans and Animals. (Exhibit D).

Copy of a MDDI Reports (Exhibit H), publisher: F-D-C Reports, Inc. dated Mar. 30, 1992, I&W7 (2 pages).

Weintraub A., (Pandian), et al.: Realtime intracardiac Two-Dimensional Echocardiography in the Catheterization Laboratory in Humans. Abstract JACC 15:No. 2: 16A, 1990, (Feb.), is attached. (Exhibit E).

Nishimura, R. A., (Tajik/Mayo), et al.: Intravascular Ultrasound Imaging: In Vitro Validation and Pathologic Correlation, JACC, 16:145–154, 1990. (Exhibit F).

Schwartz, S., (Panadian), et al.: Intracardiac Echocardiographic Guidance and Monitoring During Aoric and Mitral Balloon Valvuloplasty: In Vivo Experimental Studies. Abstract JACC, 5: No. 2: 104A, 1990, (Feb.). (Exhibit G).

Schwartz et al., "Intracardiac Echocardiography in Humans Using a Small-Sized (6F), Low Frequence (12.5 MH) Ultrasound Catheter", JACC, 21:189–198 (1993).

Primary Examiner—Francis Jaworski
Attorney, Agent, or Firm—Merchant, Gould, Smith, Edell, Welter & Schmidt

[57] ABSTRACT

A catheter having a catheter body with a proximal and distal end. The catheter including an ultrasonic transducer proximate its distal end. An access port being provided in the catheter for delivery of a therapeutic device or the like to proximate the distal end of the catheter body. A guide wire port being further provided for insertion therethrough of a guide wire.

14 Claims, 4 Drawing Sheets

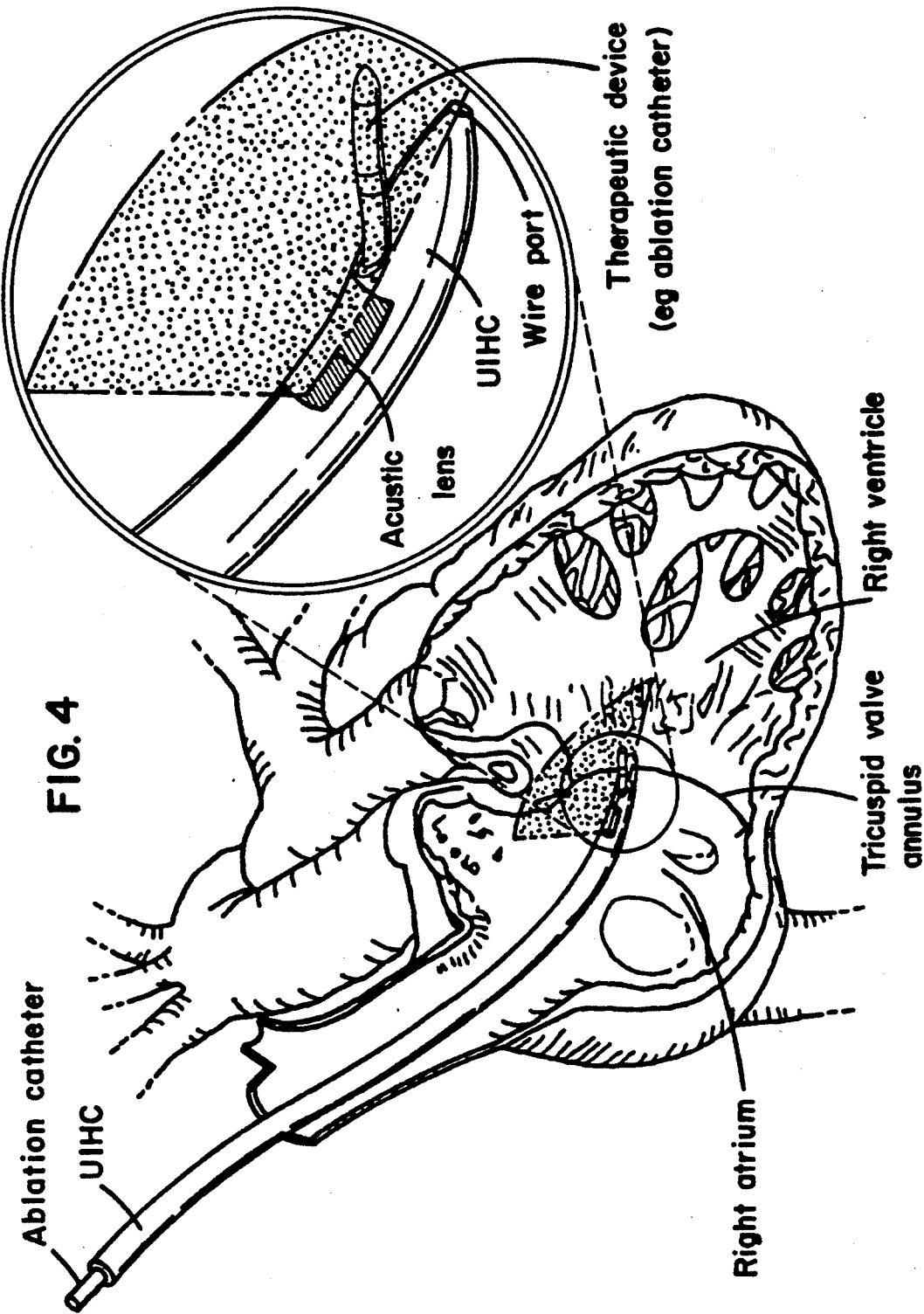

ULTRASONIC AND INTERVENTIONAL CATHETER AND METHOD

BACKGROUND OF THE INVENTION

The present invention relates to an ultrasonic and interventional catheter and method. More particularly, the present invention relates to such a catheter which provides imaging and hemodynamic capability. Further, the invention relates to such a catheter which provides transvascular and intra cardiac imaging.

Current x-ray fluoroscopy can localize radio paque devices within the cardiovascular system and outline silhouetted anatomy. Precise localization of intracardiac anatomy is not possible; e.g., directing a catheter predictably and repetitively through the same precise point within the heart.

Ultrasound (echocardiography) can be utilized to image detailed cardiac, intracardiac, and vascular anatomy. Additionally, function, hemodynamics, and visualization of blood flow is possible. Doppler echocardiography, which utilizes the physics of ultrasound frequency to determine velocity and direction of blood flow, is used to determine pressure and flow and visualize blood movement within the cardiac chambers.

Ultrasound is increasingly utilized as a substitute for cardiac catheterization.

Currently, many interventional procedures can be performed through a catheter; e.g., balloon dilation and valvuloplasty and ablation of abnormal cardiac tissue are two frequency performed procedures.

Ultrasound has recently entered into invasive applications. Transesophageal echocardiography is the most widely utilized invasive ultrasound technique. Intravascular ultrasound utilizing miniature transducers mounted on a catheter are now undergoing vigorous clinical trails. Intracardiac imaging devices have received very limited investigation.

Increasingly, therapeutic cardiac catheterization is displacing diagnostic cardiac catheterization. Thus, there is an acceptance of catheter technology as a means of altering cardiac anatomy or conduction system. Balloon angioplasty, utilization of defect closure devices, and electrical interruption of anomalous conduction pathways are now considered accepted practice. However, most of these procedures are rather gross in nature; e.g. a large balloon splitting an obstructed valve, crude devices inserted into defects, and application of thermal or electric energy to interrupt the conduction system or produce defects in septa.

SUMMARY OF THE INVENTION

The present invention relates to an ultrasonic and interventional catheter. The present invention more particularly relates to an ultrasonic and interventional catheter which provides imaging and hemodynamics, blood pressure and flow, capability. Further, the invention relates to such a catheter which images through the vascular system, i.e., transvascular and intracardiac.

In one embodiment, the present invention relates to a catheter apparatus comprising an elongated flexible body having proximal and distal ends with an ultrasonic transducer mounted proximate the distal end of the catheter body to transmit ultrasound and receive resulting echoes so as to provide a field of view within which flow rates can be measured and features imaged. An electrical conductor is disposed within the catheter body for electrically connecting the transducer to control circuitry external of the catheter. A port means is disposed in the catheter body and extends from proximate the proximal end of the catheter body to proximate the distal end of the catheter body for receiving a therapeutic device whereby a therapeutic device can be delivered to proximate the distal end of the catheter for operation within the ultrasonic transducer field of view. A guide wire port means is further disposed in the catheter body and extends from proximate the proximal end of the catheter body to proximate the distal end of the catheter body for receiving a guide wire.

The present invention further relates to a medical system comprising a catheter, control circuitry means for controlling operation of an ultrasonic transducer disposed on the catheter and display means for displaying flow rates and features imaged by the ultrasonic transducer. In one embodiment of this invention, the catheter comprises an elongated flexible body having proximal and distal ends. The ultrasonic transducer is mounted proximate the distal end of the catheter body to transmit ultrasound and receive resultant echoes so as to provide a field of view within which flow rates can be measured and features imaged. An electrical conductor is disposed in the catheter body for electrically connecting the transducer to control circuitry external of the catheter. Port means is further disposed in the catheter body and extends from proximate the proximal end of the catheter body to proximate the distal end of the catheter body for receiving a therapeutic device whereby the therapeutic device can be delivered to proximate the distal end of the catheter for operation within the ultrasonic transducer field of view. A guide wire port means is further disposed in the catheter body and extends from proximate the proximal end of the catheter body to proximate the distal end of the catheter body for receiving a guide wire.

The present invention also relates to a method of therapeutic intervention in a living body. The method includes the steps of inserting a catheter into the body, the catheter having a body with proximal and distal ends. A surgical device is inserted into the body through a port disposed in the catheter body and extending from proximate the proximal end of the catheter body to the distal end of the catheter body. An ultrasonic transducer disposed proximate the proximal end of the catheter body is pulsed to transmit ultrasound and receive resultant echoes. The surgical device is operated within a field of view provided by the ultrasonic transducer. The resultant echoes are processed to image the operation of the surgical device.

In some embodiments, a small (longitudinal), transverse, biplane or multiplane phased array ultrasound transducer is combined with a catheter delivery-system. In a preferred embodiment, the device incorporates a 5 to 10 MHz phased array transducer with a (8 French conduit) delivery port. The delivery port serves as a means to deliver other catheters (i.e., ablation catheters, etc.), record pressure and sample blood. Within the core of the ultrasound catheter there is also a 0.035 inch port for wire insertion. The completed catheter device typically might require an 18 to 24 French sheath for venous entry.

The present invention might have numerous applications. One initial application might be the ablation of right heart conduction tracts. The proposed device would be ideal for ablation of right heart bypass tracts. The tricuspid valve and its annulus could be confidently mapped by direct ultrasound visualization. An electrophysiologic catheter or ablation catheter could be passed through the port contained in the catheter. The catheter could be manipulated to its destination by use of a deflection wire disposed in the guide wire port. Precise mapping and intervention can then be carried out under direct ultrasound visualization.

Other applications include ultrasound guided myocardial biopsy, surgical implantation and/or removal of devices under ultrasound control, and transvascular diagnosis of perivascular and organ pathology.

The present invention provides an intravascular ultrasound catheter capable of catheter-based intervention while under visual observation. Avoidance of major surgical procedures in conjunction with precision catheter intervention is a substantial improvement over present patient care.

These and various other advantages and features of novelty which characterize the invention are pointed out with particularity in the claims annexed hereto and forming a part hereof. However, for a better understanding of the invention, its advantages and objects obtained by its use, reference should be made to the drawings which form a further part hereof, and to the accompanying descriptive matter, in which there is illustrated and described a preferred embodiment of the invention.

BRIEF DESCRIPTION OF THE DRAWINGS

A better understanding of the construction and operational characteristics of a preferred embodiment(s) can be realized from a reading of the following detailed description, especially in light of the accompanying drawings in which like reference numerals in the several views generally refer to corresponding parts.

FIG. 4 is an illustration illustrating an application of a catheter in accordance with the principles of the present invention.

DETAILED DESCRIPTION OF A PREFERRED EMBODIMENT

Figure 1:
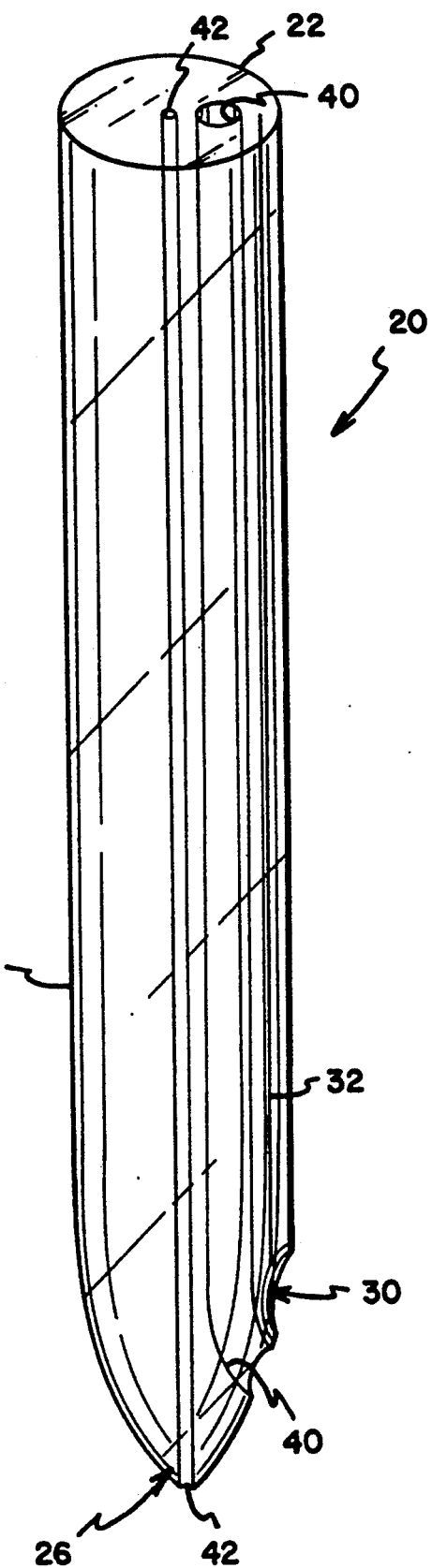
FIG. 1 is a partial perspective view of an embodiment of a catheter in accordance with the principles of the present invention.
Figure 2:
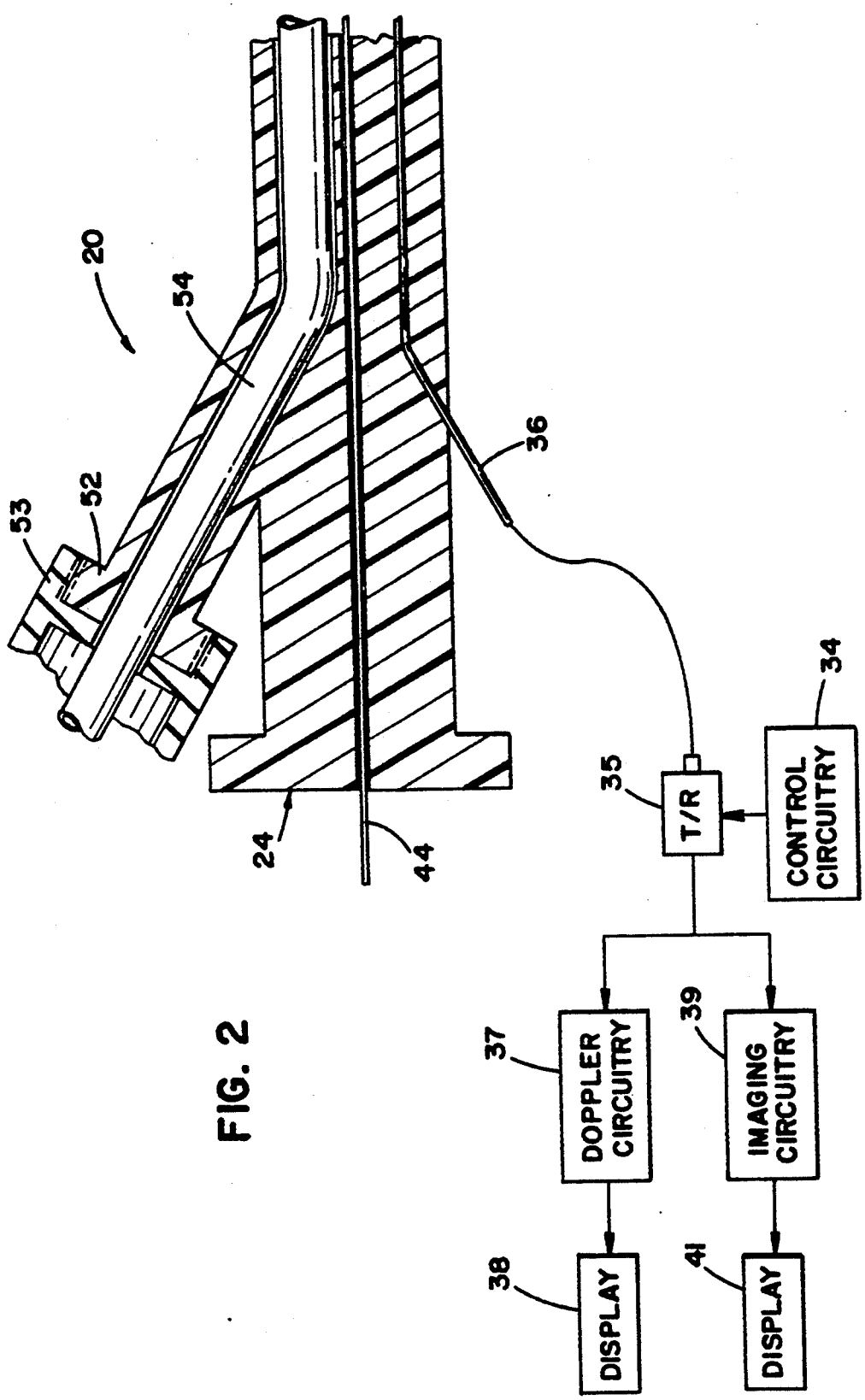
FIG. 2 is a block diagram in part and sectional diagram in part illustrating an embodiment of a system utilizing the catheter shown in FIG. 1.
Figure 3:
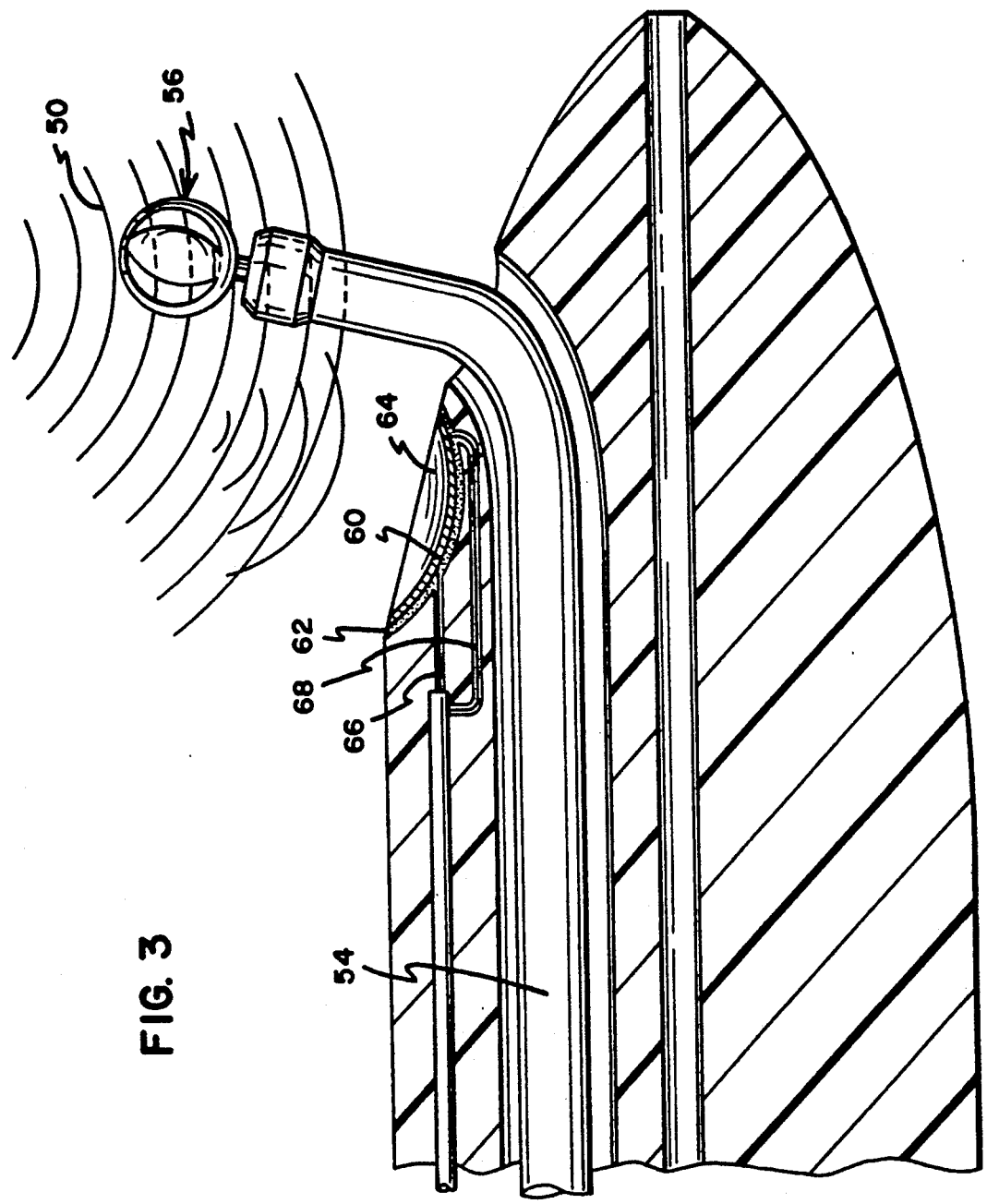
FIG. 3 is an enlarged cross-sectional view taken proximate the proximal end of the catheter shown in FIG. 1.

Referring now to FIGS. 1-3, there is generally illustrated by reference numeral 20 a catheter in accordance with the principles of the present invention. As shown, the catheter 20 includes an elongated flexible plastic tubular catheter body 22 having a proximal end 24 and a distal end 26. The catheter includes proximate its longitudinal distal end 26 a phased array ultrasonic transducer 30 which is used to transmit ultrasound and receive resultant echoes so as to provide a field of view within which flow rates can be measured and features imaged. An electrical conductor 32 is disposed in the catheter body 22 for electrically connecting the transducer 30 to control circuitry 34 external of the catheter body 22. An access port 40 is disposed in the catheter body 22 and extends from proximate the proximal end 24 of the catheter body 22 to proximate the distal end 26 of the catheter body 22. The access port is configured to receive a therapeutic device, such as a catheter, medication, sensors, etc. so as to enable such items to be delivered via the access port 40 to the distal end 26 of the catheter body 22 for operation within the ultrasonic transducer field of view. Such items might be used for intervention; e.g., ablation catheter, surgical device, etc., monitoring blood pressure, sampling blood, etc. A guide wire access port 42 is also disposed within the catheter body 22 and extends from proximate the proximal end 24 of the catheter body 22 to proximate the distal end 26 of the catheter body 22 for receiving a guide wire 44.

In the preferred embodiment of the present invention, the ultrasonic transducer preferably has a frequency of 5 to 20 megahertz (MHz) and more preferably a frequency of 7 to 10 MHz. Intracardiac imaging in an adult will require image penetration of up to 2 to 10 centimeters (cm). In the preferred embodiment, the catheter body 22 preferably has a diameter of 4 to 24 French [one French divided by Pi equals one millimeter (mm)] and, more preferably a diameter of 6 to 12 French. In the preferred embodiment, the access port 40 has a diameter of 7 to 8 French and the guide wire port 42 has a diameter of 0.025 to 0.038 inches.

As generally illustrated FIG. 2, the catheter 20 of the present invention can be utilized in a medical system including the appropriate control circuitry 34 for controlling operation of the ultrasonic transducer. As illustrated in FIG. 2, the control circuitry is electrically interconnected to transceiver circuitry (T/R) 35 for receiving and transmitting signals via a cable 36 to the ultrasonic transducer 30. In turn, the transceiver circuitry 35 is electrically interconnected to Doppler circuitry 37 and an appropriate display device 38 for displaying hemodynamics or blood flow. In addition, the transceiver circuitry 35 is electrically interconnected to suitable imaging circuitry 39 which is interconnected to a display 41 for displaying images.

During operation, the control circuitry might be designed to cause the ultrasonic transducer 30 to vibrate so as to cause an appropriate ultrasound wave to project from proximate the distal end 26 of the catheter body 22. The ultrasound wave, represented by lines 50 in FIG. 3, will propagate through the blood surrounding the distal end 26 and a portion of the body structure. A portion of the ultrasound wave so transmitted will be reflected back from both the moving red blood cells and the like and the body structures to impinge upon the transducer 30. An electrical signal is thereby generated and transmitted by the cable 36 to the input of the transceiver 35. A signal might then be transmitted to the Doppler circuitry 37 which will include conventional amplifying and filtering circuitry commonly used in Doppler flow metering equipment. The Doppler circuitry 37 will analyze the Doppler shift between the transmitted frequency and the receive frequency to thereby derive an output proportional to flow rate. This output may then be conveniently displayed at the display 38 which might be a conventional display terminal. Accordingly, the user will be able to obtain a readout of blood flow rates or hemodynamic information.

In order to obtain imaging information, the control circuitry 34 will likewise trigger the ultrasonic transducer 30 via the transceiver 35 to vibrate and produce an ultrasound wave. Once again, a portion of the wave or energy will be reflected back to the ultrasonic transducer 30 by the body features. A corresponding signal will then be sent by the cable 36 to the transceiver circuitry 35. A corresponding signal is then sent to the imaging circuitry 39 which will analyze the incoming signal to provide, at the display 41, which also might be a conventional display apparatus, an image of the body features.

This imaging can occur while a therapeutic or surgical device is being used at the distal end 26 of the catheter within the field of view provided by the ultrasonic transducer 30. Accordingly, the user will be able to monitor his/her actions and the result thereof.

As illustrated in FIG. 2, the catheter body 22 might include proximate its proximal end 24 a suitable mounting structure 52 to the access port 40. A therapeutic or surgical device structure 53 might be suitably attached to the structure 52 by suitable means, e.g., threaded, etc.. As illustrated, an elongated cable-like member 54 will extend along the access port and slightly beyond the distal end 26 of the catheter body 22 wherein an operative portion 56 of the surgical tool might be interconnected.

Additional detail of the distal end 26 of the catheter body 22 is illustrated in FIG. 3. As illustrated in FIG. 3, the ultrasonic transducer 30 might include a piezo electric polymer such as Polyvinylidenedifloride (PVDF) 60 which is bonded by an epoxy layer 62 to a depression 64 approximate the distal end 26. Individual wires 66 and 68 are illustrated as interconnecting the electrodes 70 and 72. Although some detail is provided with respect to an embodiment of an ultrasonic transducer which might be used, it will be appreciated that various types of transducers having various configurations and orientations might be utilized in keeping with the present invention.

As illustrated in FIG. 3, the operational portion 56 of the therapeutic device is illustrated as generally being capable of operation in the field of view of the ultrasonic transducer 30. Accordingly, it is possible for the user to monitor operation of the therapeutic device by use of the ultrasonic transducer. Moreover, it is possible for the user to monitor the features of the body within the field of view, both before, during and after interventional activity.

In use, the user would insert the catheter body 22 into the body via the appropriate vascular access to the desired location in the body, such as selected venous locations, heart chamber, etc. In one approach, a guide wire might be first inserted into place and then the catheter body fed along the guide wire. The user might then insert a surgical device into the body through the access port 40 and feed the surgical device to proximate the proximal end 26 of the catheter body 22. Prior to, during and after operation of the surgical device, the user might obtain both hemodynamic measurements and images from the ultrasonic transducer field of view. By operation of the surgical device within the field of view of the transducer 40, the user can monitor operation of the surgical device at all times.

I. Catheter features:

This disclosed catheter has the following detailed features:

A. Ultrasound frequency: The proposed device optimally uses a 5 to 20 mHz transducer with the most optimally applied frequency of 7 to 10 mHz. The lower frequency used in the UIHC reflects the need to image larger objects such as the cardiac septa, valves, and extravascular anatomy.

B. Catheter size: Catheter diameters will generally be larger than intravascular catheters and will range 4 to 24 French with the optimal catheter diameter 6 to 12 French (French size=French divided by Pi plus millimeter diameter).

C. Intervention: One primary function of this catheter system is to guide the logical and safe use of various a) ablation, b) laser, c) cutting, d) occluding, e) etc., catheter-based interventional cardiovascular tools. The invention has the access port through which other technologies (devices) can be passed. Once the interventional tool exits the catheter tip, it can be directed repeatedly and selectively to specific site for controlled intervention.

D. Imaging: The invention is also an imaging system capable of visualizing intracardiac, intravascular, and extravascular structures. Because the transducer frequencies utilized are relatively low compared to intravascular systems, the catheter 20 can see multiple cardiac cavities and visualize structures outside the vascular system. The imaging capability is basically two-fold: 1) diagnostic and 2) application.

1. Diagnostic imaging: The catheter 20 can effectively perform diagnostic intracardiac and transvascular imaging. This application will more than likely be performed just prior to an interventional application. The intervention then will follow using the same catheter system and its unique delivery capability. Some examples of diagnostic imaging include 1) accurate visualization and measurement of an intracardiac defect, 2) characterization of valve orifice, 3) localization of a tumor and its connections, 4) etc. Extravascular diagnoses would include 1) visualize pancreatic mass/pathology, 2) retroperitoneal pathology, 3) intracranial imaging, 4) recognition of perivascular pathology, and 5) etc.

2. Application imaging refers to the use of the catheter and its imaging capability to deliver and then apply another technology such as 1) occlusion device for closure of a septal defect, 2) ablation catheters for treatment of bypass tracts, 3) creation of a defect such as that with the blade septostomy catheter or laser-based catheter system, and 4) directing of valvuloplasty, etc. By direct imaging of an application, such as ablation, the procedure will be able to be performed more safely and repeatedly, and the result can be better assessed.

E. Hemodynamics: The catheter 20 is a truly combined ultrasound Doppler and conventional hemodynamic catheter. There are Doppler catheters, and there are catheters capable of imaging and measuring hemodynamic pressure. However, the catheter 20 is capable of Doppler hemodynamics (continuous and pulsed-wave Doppler) as well as high-fidelity hemodynamic pressure recording while simultaneously imaging the heart and blood vessel. The catheter 20 provides a combination of imaging, hemodynamic, and interventional delivery catheter.

II. Analogy with other existing therapeutic technologies:

Like interventional peritoneoscopy, intracardiac ultrasound capable of 1) imaging, 2) delivering a therapeutic device, and 3) obtaining simultaneous hemodynamics which can be used to develop less invasive cardiac surgical techniques. This simultaneous use of one or more devices within the heart or vascular tree opens up the potential to develop less invasive surgical therapies. Examples would include 1) removal of a cardiac tumor by visually grasping the tumor with one device and visually cutting its attachment with a second device, thus allowing less invasive extraction of intracardiac mass lesions, 2) visually placing an electrophysiologic catheter on a bypass tract and then with direct ultrasound visualization ablate the underlying tract with the second device, 3) visually performing laser surgery such as creating an intraatrial defect, vaporization of obstructing thrombus such as is seen in pseudointimal occlusion of conduits, 4) visually removing a foreign body from the heart or vascular tree, and 5) directing intravascular surgery from within a blood vessel or monitoring concomitant hemodynamic changes.

III. Selected applications include the following:

A. Radio frequency ablation: Presently a bypass tract is localized by an electrophysiologic study which systematically maps the atrioventricular valve annulus. Positioning of the ablation catheter is determined by x-ray fluoroscopy and certain electrical measurements which relate the distance of the ablation catheter from a reference catheter. The catheter 20 will allow an operator to map the atrioventricular valve under direct ultrasound visualization. Thus, increased accuracy of catheter placement, precision of the applied therapy, and immediate assessment of outcome would result.

The above ablation technique would be particularly applicable for right-sided bypass tracts (in and around the tricuspid valve annulus). This would be accomplished by placement of the catheter 20 through the superior vena cava above the tricuspid annulus.

For left-sided bypass tracts, the catheter 20 could be placed across the atrial septum under direct ultrasound visualization. The mitral annulus could thus be mapped directly and the localized bypass tract precisely ablated under visual ultrasonic and hemodynamic direction. Complications such as valve perforation, multiple imprecise applications of ablation energy, and inadvertent ablation of normal conduction tissue would be substantially reduced.

Ablation of bypass tracts would be an ideal utilization of the proposed ultrasonic interventional catheter system.

B. Cardiac biopsy: In the era of safe cardiac biopsy, there is a need for precision biopsy. Ultrasound direction of the biopsy device to an intracardiac tumor, avoidance of scar, and selective biopsy of suspect tissue are feasible with the catheter 20 device. One of the more frequently life-threatening complications in the cardiac catheterization laboratory is catheter perforation of the heart. Such complications most commonly accompany cardiac biopsy, electrophysiologic catheter manipulation, and valvuloplasty. Use of an intracardiac ultrasound imaging, hemodynamics, and delivery catheter should substantially increase or improve safety of these procedures.

C. Transvascular diagnoses: The catheter 20 will allow visualization of perivascular and extravascular pathology. Transvascular or transorgan imaging and localization of pathology out of the immediate vascular tree will result in a substantial step forward in the diagnosis and possible treatment of difficult to reach pathology. The catheter 20 cannot only diagnose but guide a biopsy needle and therapeutic device to an extravascular lesion in question. The retroperitoneum, mediastinum, and basal cerebrovascular pathology are logical areas of interest. Accurate characterization of various pathologies will be more feasible. Every organ has its own vascular system, and the proposed ultrasound transvascular system is an ideal tool to assess difficult to reach areas of the body. The vascular system is a conduit to each organ, and the catheter 20 can be delivered to each organ. Characterization of the underlying parenchyma and possible transvascular biopsy or treatment will ultimately be developed.

D. Ultrasound manipulation of therapeutic devices within the heart and blood vessels: The catheter 20 opens the potential not only to visualize but to directly intervene with the same catheter system. There are numerous intraoperative catheter-based systems which to date use conventional x-ray to accomplish their goal of placement and application of a specified therapy. There is a need for a device which can more precisely guide such catheter-based systems. It is too expensive and technically impractical to incorporate ultrasound into every catheter-based technology. The catheter 20 has all the prerequisites of an ideal imaging and interventional instrument and has the ability to 1) image, 2) obtain hemodynamics by multiple means (pressure dynamics and Doppler, 3) function as a diagnostic as well as therapeutic device, and 4) accommodate other unique technologies which would enhance the application of both systems.

E. Expanding applications of technologies: The catheter 20 is a new and exciting innovation to invasive medicine. There are multiple other and yet-to-be-determined applications. However, the new concept described opens the potential development of less expensive, more precise, and safe intravascular and transvascular diagnostic and surgical devices.

IV. Summary:

The catheter 20 is very much different from any conventional ultrasound catheter-based system. The catheter 20 incorporates image and hemodynamic capability as well as the ability to deliver other diverse technologies to specified sites within the cardiovascular system (heart and blood vessels). The catheter 20 is seen as an ideal diagnostic and therapeutic tool for future development. The proposed applications foster greater preciseness, adaptability, and safety. Ultrasound permits visualization from within blood-filled spaces as well as through blood-filled spaces into other water- or fluid-filled tissue. The catheter 20 will evolve into the ultimate interventional system.

FIG. 4 is an illustration showing one potential use of the ultrasound imaging and hemodynamic catheter (UIHC). In this particular example, the UIHC is advanced from the superior vena cava to the tricuspid valve annulus. Simultaneously visualized in the annulus, electrophysiologic and ultimately and ablation procedure are performed. The ability to directly visualize and direct therapeutic catheter devices highlights only one of the many applications of the UIHC.

It is to be understood, however, that even though numerous characteristics and advantages of the present invention have been set forth in the foregoing description, together with details of the structure and function of the invention, the disclosure is illustrative only, and changes may be made in detail, especially in matters of shape, size and arrangement of parts within the principles of the invention to the full extent indicated by the broad general meaning of the terms in which the appended claims are expressed.

What is claimed is:

1. A catheter apparatus, comprising:
    an elongated flexible body having proximal and distal ends;
    an ultrasonic transducer mounted proximate the distal end of the catheter body to transmit ultrasound and receive resultant echoes so as to provide a field of view within which flow rates can be measured and features imaged, an electrical conductor disposed in the catheter body for electrically connecting the transducer to control circuitry external of the catheter;

port means disposed in the catheter body and extending from proximate the proximal end of the catheter body to proximate the distal end of the catheter body for receiving a therapeutic device whereby the therapeutic device can be delivered to proximate the distal end of the catheter for operation within the ultrasonic transducer field of view, an operational end of the therapeutic device projecting from proximate the distal end of the catheter body into the ultrasonic transducer field of view so as to allow visualization of the therapeutic device during its operation; and guide wire port means disposed in the catheter body and extending from proximate the proximal end of the catheter body to proximate the distal end of the catheter body for receiving a guide wire.

2. An apparatus in accordance with claim 1, wherein the ultrasonic transducer has a frequency of 5 to 20 mHz.

3. An apparatus in accordance with claim 1, wherein the ultrasonic transducer has a frequency of 7 to 10 mHz.

4. An apparatus in accordance with claim 1 wherein the catheter body has a diameter of 4 to 24 French.

5. An apparatus in accordance with claim 1 wherein the catheter body has a diameter of 6 to 12 French.

6. An apparatus in accordance with claim 1 wherein the port means has a diameter of 7 to 8 French.

7. A medical system, comprising:
 a catheter, comprising an elongated flexible body having proximal and distal ends;
 an ultrasonic transducer mounted proximate the distal end of the catheter body to transmit ultrasound and receive resultant echoes so as to provide a field of view within which flow rates can be measured and features imaged, an electrical conductor disposed in the catheter body for electrically connecting the transducer to control circuitry external of the catheter;
 port means disposed in the catheter body and extending from proximate the proximal end of the catheter body to proximate the distal end of the catheter body for receiving a therapeutic device whereby the therapeutic device can be delivered to proximate the distal end of the catheter for operation within the ultrasonic transducer field of view, an operational end of the therapeutic device projecting from proximate the distal end of the catheter body into the ultrasonic transducer field of view so as to allow visualization of the therapeutic device during its operation;
 guide wire port means disposed in the catheter body and extending from proximate the proximal end of the catheter body to proximate the distal end of the catheter body for receiving a guide wire;
 control circuitry means for controlling operation of the ultrasonic transducer; and
 display means for displaying the flow rates and the features imaged by the ultrasonic transducer.

8. An apparatus in accordance with claim 7, wherein the ultrasonic transducer has a frequency of 5 to 20 mHz.

9. An apparatus in accordance with claim 7, wherein the ultrasonic transducer has a frequency of 7 to 10 mHz.

10. An apparatus in accordance with claim 7, wherein the catheter body has a diameter of 4 to 24 French.

11. An apparatus in accordance with claim 7 wherein the catheter body has a diameter of 6 to 12 French.

12. An apparatus in accordance with claim 7 wherein the port means has a diameter of 7 to 8 French.

13. A method of therapeutic intervention in a living body; comprising:
 inserting a catheter into the body, the catheter having a body with a proximal and distal end;
 inserting a surgical device into the body through a port disposed in the catheter body and extending from proximate the proximal end to the distal end of the catheter body;
 projecting the surgical device out of the catheter body from proximate the distal end of the catheter body;
 pulsing an ultrasonic transducer, disposed proximate the proximal end of the catheter body, to transmit ultrasound and receive resultant echoes;
 operating the surgical device within a field of view provided by the ultrasonic transducer, an operational end of the surgical device projecting from proximate the distal end of the catheter into the ultrasonic transducer field of view so as to allow visualization of the therapeutic device during its operation; and
 processing the resultant echoes to image the operation of the surgical device.

14. A method in accordance with claim 13, comprising the further step of analyzing the resultant echoes with doppler circuitry to provide hemodynamic information.

* * * * *